US007678442B2

(12) United States Patent
Casey et al.

(10) Patent No.: US 7,678,442 B2
(45) Date of Patent: Mar. 16, 2010

(54) EMBOSSED NON-WOVEN FABRIC HAVING A THREE-DIMENSIONAL STRUCTURE

(75) Inventors: William A. Casey, Andover, MA (US); Claudio Suarez, Buenos Aires (AR)

(73) Assignee: Karl Freudenberg KG, Weinheim (DE)

( * ) Notice: Subject to any disclaimer, the term of this patent is extended or adjusted under 35 U.S.C. 154(b) by 945 days.

(21) Appl. No.: 10/496,048

(22) PCT Filed: Nov. 18, 2002

(86) PCT No.: PCT/EP02/12903

§ 371 (c)(1),
(2), (4) Date: Sep. 2, 2004

(87) PCT Pub. No.: WO03/043806

PCT Pub. Date: May 30, 2003

(65) Prior Publication Data

US 2005/0008825 A1 Jan. 13, 2005

(30) Foreign Application Priority Data

Nov. 21, 2001 (AR) .............................. P010105436

(51) Int. Cl.
*B32B 3/00* (2006.01)
*A61F 13/15* (2006.01)

(52) U.S. Cl. ....................... 428/156; 428/172; 428/213; 156/209; 264/257; 425/194; 604/385.01

(58) Field of Classification Search ................. 428/174, 428/175, 156, 172, 213; 264/257, 319; 156/209; 425/194, 363, 367; 604/385.01
See application file for complete search history.

(56) References Cited

U.S. PATENT DOCUMENTS 1,189,140 A * 6/1916 Lane .......................... 428/154
3,616,157 A 10/1971 Smith .......................... 161/124
3,717,532 A 2/1973 Kamp .......................... 156/199
3,839,137 A * 10/1974 Davis et al. ................. 428/183
3,843,470 A * 10/1974 Betley et al. ................ 162/343
4,592,943 A * 6/1986 Cancian et al. ............. 428/171
4,631,221 A * 12/1986 Disselbeck et al. .......... 428/166

(Continued)

FOREIGN PATENT DOCUMENTS

DE 19725749 12/1998

(Continued)

*Primary Examiner*—Donald Loney
(74) *Attorney, Agent, or Firm*—Davidson, Davidson & Kappel, LLC

(57) ABSTRACT

A three-dimensionally embossed non-woven fabric, which is comprised of fibers and/or filaments (3) oriented primarily in the moving direction (2) of the machine, and has zones (5, 7) with regularly alternating elevations (4*a*, 8*a*) and indentations (4*b*, 8*b*), which are separated from one another by non-embossed areas (6) that are continuous in the moving direction (2) of the machine. These non-embossed areas constitute a proportion ranging from 5% to 50% with regard to the entire surface of the non-woven fabric (1) and the elevations (4*a*, 8*a*), and indentations (4*b*, 8*b*), when viewed from the opposite side, form indentations or elevations respectively, whereby the surfaces (10*a*, 10*b*) delimited by the elevations give the non-woven fabric an apparent thickness ranging from 0.5 mm to 5.5 mm.

30 Claims, 7 Drawing Sheets

U.S. PATENT DOCUMENTS

| | | | | |
|---|---|---|---|---|
| 5,366,785 | A * | 11/1994 | Sawdai | 428/156 |
| 5,731,062 | A * | 3/1998 | Kim et al. | 428/175 |
| 6,733,626 | B2 * | 5/2004 | Ruthven et al. | 162/114 |

FOREIGN PATENT DOCUMENTS

| | | | |
|---|---|---|---|
| EP | 0499942 | A2 | 8/1992 |
| EP | 0809991 | A1 | 12/1997 |
| EP | 0810078 | | 12/1997 |
| EP | 0631768 | B1 | 4/1998 |
| EP | 0976373 | A1 | 2/2000 |
| EP | 0976374 | A1 | 2/2000 |
| EP | 0976375 | A1 | 2/2000 |
| EP | 1047821 | A1 | 11/2000 |
| EP | 1047822 | A1 | 11/2000 |
| EP | 1047823 | A1 | 11/2000 |
| EP | 1047824 | A1 | 11/2000 |
| RU | 2145204 | | 2/2000 |

* cited by examiner

EMBOSSED NON-WOVEN FABRIC HAVING A THREE-DIMENSIONAL STRUCTURE

The present invention relates to an embossed, open-pore non-woven fabric having a three-dimensional structure, a method for its manufacture and a device used with it. The non-woven fabric is made up of regularly alternating areas having molded, weight-thinned three-dimensional elevations and non-molded, flat zones having an unchanged weight.

The present invention also relates to a special embossing method and the roller geometry required for it in order to impart the special 3D embossed structure to the non-woven fabric after its passage through the press gap of two engaged positive and negative rollers.

BACKGROUND

The absorbent core of infant diapers, incontinence and feminine hygiene products is today covered by at least two layers on the side worn next to the body. Between the cover non-woven fabric or the perforated film and the absorbent core is positioned an acquisition and distribution layer (ADL) of non-woven fabric or reticulated foam, which as the name implies, quickly takes up the body fluid (urine, thin feces or menses) and distributes it as uniformly as possible to the absorbent core lying under it, which is normally made of cellulose and super absorbent powder. This keeps the human skin dry, thus preventing skin irritation as well as leakage of the body fluid at the sides. The back of the absorbent hygiene product is sealed against permeation of body fluid by a water-tight film or a non-woven-film laminate.

Non-woven fabrics bonded thermally in a hot air dryer or non-woven fabrics of crimped, relatively coarse denier fibers bonded by polymer dispersions are known for use in ADLs. The fibers have deniers greater than 3.3 dtex and are made up primarily of polyester (polyethylene terephthalate) and/or polyolefins, bicomponent fibers having a side-by-side or a core/jacket structure being used for fiber bonding in the through-flow oven and one of the two fiber components being melted significantly more deeply than the other component. In relation to their low weight, such non-woven fabrics have a relatively high bulk (thickness). It is known, however, that this initial thickness is already significantly reduced when the product is rolled up under stresses ordinarily used and the pressure conditions in the packaging contribute further to the reduction in thickness.

For that reason, means have been sought to achieve a thickness not only by using crimped fibers having a more or less statistical distribution and their bonding but also to bring such crimped non-woven fabrics into the third dimension, which we will consistently describe as the Z-direction in the following, by undulation or other geometric orientations. It has been shown that this makes it possible to attain higher compression resistances than by using high-loft non-woven fabrics with the consequence of significantly reduced loss of thickness when a diaper passes through the production steps, including packaging and storage.

An embossing method for manufacturing a structured, bulky non-woven fabric is described in DE 197 25 749 A1. A pre-bonded spun non-woven fabric, the endless filaments of which have been drawn to only 50% to 70% of the maximum possible draw ratio, are subjected to a particular finishing treatment. In doing so, the spun non-woven fabric is passed between a positive roller having a knobby surface and a negative roller having lamellar strips positioned transverse to the machine direction, the strips meshing with the channels kept open by the knobs. This results in 3D non-woven fabrics having areas of conically shaped weight-thinned elevations that are surrounded by linear, undeformed areas.

The disadvantage of the embossing method described in DE 197 25 749 A1 is that it is limited to undrawn or partially drawn endless filament non-woven fabrics (spun non-woven fabrics). Such non-woven fabrics are made from coarse-denier, uncrimped endless fibers that are known to result in hard, rough and non-textile products and therefore are not used as ADLs in diapers. Such endless filaments having a side-by-side structure or an asymmetric core/jacket structure do not result in crimping in a partially drawn state. Such crimping is ordinarily triggered by subsequent thermal processing, which in turn—as is known to those skilled in the art—prevents drawability (or formability) due to the crystallization which has occurred. Consequently, the prerequisites for the applicability of the embossing method described in DE 197 25 749 A1 are lacking.

A fluid distribution material having improved fluid distribution properties is described in EP-B 0.809.991 and EP-A 0.810.078. In this case, a plastically deformable web is formed into a non-woven fabric having a 3D structure by passing it through a pair of negative/positive rollers. A variation of the two applications referenced above is the embossed material and method for it, which is described in EP-B 0.499.942. However, such structures similar to corrugated cardboard have the disadvantage that they do not withstand any sustained pressure loads.

In EP applications 1.047.824, 1.047.823, 1.047.822 and 1.047.821, non-woven fabrics having elevations and indentations are produced in an intermediate step by passing the sheet material over two heated toothed gear rollers. The ribbings have little compression stability based on the fact that they lack a non-stabilizing fabric, which is glued to one side of the elevations or stiffenings. In the patent applications cited, it is rather the case that the undulations must be removed to the greatest possible extent or partially removed to produce soft and slightly elastic products transverse to the undulation.

Absorbent disposable items having a fecal management layer are known from EP-A 0.976.375, EP-A 0.976.374 and EP-A 0.976.373, the latter being made from an undulated non-woven fabric to which a flat non-woven fabric backing (EP-A 0.976.375) is cemented. Thick polymer filaments (EP-A 0.976.374) or meshed fabrics (EP-A 0.976.37) may be used instead of the non-woven fabric backing. Such undulated non-woven fabric laminates stabilized by a backing have proven to be suitable ADLs for fecal management and improved urine management. However, the production of such 3D laminate structures is very elaborate and requires two components and an additional adhesive in many cases. However, the use of a thick monofilament (having a denier in the range of several thousand dtex) proved to be unsuitable because such monofilaments are undrawn (or come from a hole-type nozzle) and therefore stretch under the strong mechanical load in the machine direction in diaper production with thinning of the filament and thus have an unacceptable property in this respect.

BRIEF SUMMARY OF THE INVENTION

An object of the present invention is to eliminate the aforementioned disadvantages of the related art and to provide an embossed non-woven fabric, which returns to its original shape after a previous compression better than the previously known embodiments without the requirement of an additional stabilizing layer, and is consequently better suited for the uptake of liquids of varying composition or the transport of the liquids into an absorbent layer. An alternate or additional object of the present invention is furthermore to provide a method for manufacturing a non-woven fabric and a device suitable for implementing the method. In particular, an embossing device may be offered to diaper manufacturers as an addition to a diaper production line, the device permitting the manufacturer to convert an unembossed, two-dimensional non-woven fabric inline with the diaper production into the form of an embossed, three-dimensional non-woven fabric having an improved liquid acquisition and distribution function and to place it in a diaper or a wound dressing. Moreover, it should be possible to produce the non-woven fabric independently of the diaper production, and the non-woven fabric should have the aforementioned properties largely unchanged after an intermediate storage in rolled-up condition.

According to the present invention, the three-dimensionally embossed non-woven fabric is made up of fibers and/or filaments 3 oriented in machine direction 2 and zones 5, 7 having regularly alternating elevations 4*a*, 8*a* and indentations 4*b*, 8*b*, which are separated from one another by unembossed, continuous areas 6 in machine direction 2, the unembossed areas making up a proportion ranging from 5% to 50% in relation to the entire surface of non-woven fabric 1 and elevations 4*a*, 8*a* and indentations 4*b*, 8*b*, when viewed from the opposite side, forming indentations and elevations, respectively, the surfaces defined by the elevations imparting an apparent thickness ranging from 0.5 mm to 5.5 mm to the non-woven fabric.

The present invention describes a non-woven fabric of staple fibers in which partial surface areas have regularly alternating elevations and indentations (peaks/valleys) in the machine direction and each row of elevations/indentations is interrupted by an unshaped linear area. The unshaped linear areas are positioned symmetrically to asymmetrically to the elevations and valleys of the adjacent areas in the three-dimensionally formed non-woven fabric. In a preferred embodiment, the areas formed into peaks and valleys extend symmetrically along the unshaped linear area.

The row of adjacent formed areas transverse to the machine direction is situated in such a way that there is always a gap to the adjacent row of undulations.

The undulations extend exactly in the machine direction.

The method of the present invention for manufacturing a non-woven fabric is such that fibers and/or filaments 3 oriented primarily in machine direction 2 are laid down on a gauze, reinforced and formed into a three-dimensional non-woven fabric by a treatment using embossing rollers at temperatures ranging from 65° C. to 160° C.

The staple fibers of the two-dimensional non-woven fabric for the 3D embossing are laid down in the machine direction. The fiber gauze may be additionally reoriented along this preferred direction using a compression device.

The staple fibers of the staple fiber gauze laid down in the machine direction are crimped two-dimensionally and/or three-dimensionally.

The fibers are made from fiber polymers that have a high restoring force in relation to mechanical forces. Polyethylene terephthalate fibers having a denier ranging from 3.3 to 30 dtex, preferably however, 6.7 to 18 dtex have proven to be suitable in particular. Fibers of different deniers may be blended.

The staple fiber gauzes are either bonded adhesively by using aqueous polymer dispersions according to known methods, by thermal fiber/fiber bonding in a forced air oven, or by application of heat and pressure in a pair of calender rolls. In the case of passage through a forced air oven, bicomponent fibers are added to the hydrophilic fibers as binding fibers.

The non-woven fabric presented for embossing contains a hydrophilic, easy-to-wet surface-active agent (surfactant), which is either applied into or on the fiber by the fiber manufacturer and/or is applied to the non-woven fabric later and/or is introduced into the non-woven fabric with the polymer dispersion preparation used. The surfactant may have a varying degree of bonding to the fibers and may thus be removable by washing or semi-permanent to completely permanent against the contact of body fluid.

In the case of an adhesive bond, an aqueous polymer dispersion based on a butadiene copolymer such as styrene-butadiene or acrylonitrile-butadiene copolymer is used. The binding agent is preferably free from cross-linking components and after application remains in the non-woven fabric in a thermoplastically deformable condition. The Shore hardness A of the binder film cast from the dispersion is in the range of approximately 70-100, preferably 75-95.

The cross-section of the staple fibers may have varying forms such as round, oval, trilobal, square, rectangular. The fiber polymer may be distributed over the entire fiber cross-section in the same thickness. However, the fiber may also be internally hollow, it being possible for the hollow space to make up 10%-30% of the fiber.

All crimped single component synthetic fibers that do not shrink or even melt under the embossing conditions are suitable for the embossing method of the present invention. The crimped synthetic fibers may also be blended with undrawn, uncrimped fibers, however, at a proportion <50%.

The base material to be formed into a 3D structure preferably contains polyester fibers if an aqueous dispersion is used for the non-woven fabric bonding. The fiber: binder ratio is approximately 20:80 to 40:60. The binding agent may be applied using known application methods such as foam impregnation, one-sided slop padding or wet-in-wet printing. The binding agent may be uniformly distributed over the cross-section of the non-woven fabric or it may have a binding agent applied quantity gradient from one side to the other. The drying temperatures and retention times in the dryer must be selected in such a way that a complete filming of the polymer takes place. This may be determined by the transparency (of the unpigmented binder agent) of the binding points.

The staple fiber gauze of the precursor may be made up of one or as many as three plies. The average denier of the three plies preferably increases from one ply to the next adjacent ply. After the 3D formation, the multi-ply non-woven fabric having the coarsest (highest denier) gauze side is positioned in the diaper as an ADL facing the underside of the non-woven cover fabric. In the case of an embossed non-woven fabric having binding agent distribution gradients, the side having more binding agent is in contact with the absorbent core or with the hydrophilic meltblown non-woven fabric or tissue paper (core wrap) enveloping it.

The device of the present invention for implementing the method includes at least two embossing rollers 21, 22, which mesh in such a way that a non-woven fabric 20 is guided between them and formed, embossing rollers 21, 22 being made up of toothed wheels 11, separated by spacers 12 on a shaft 13.

BRIEF DESCRIPTION OF THE DRAWINGS

The present invention will be described in greater detail with reference to the figures.

DETAILED DESCRIPTION

Figure 1:
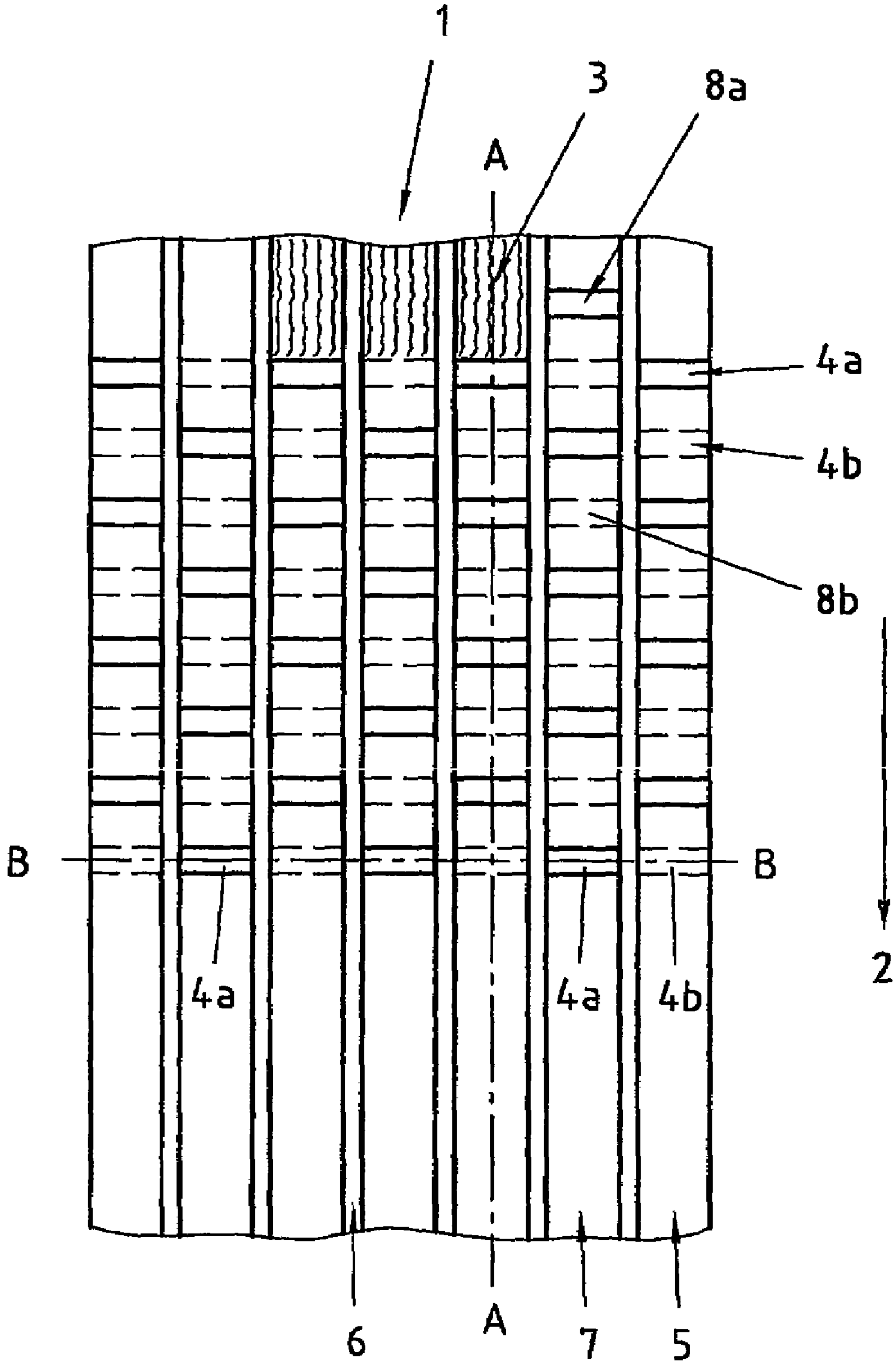
FIG. 1 shows a top view of a three-dimensional non-woven fabric formed according to the present invention
Figure 2:
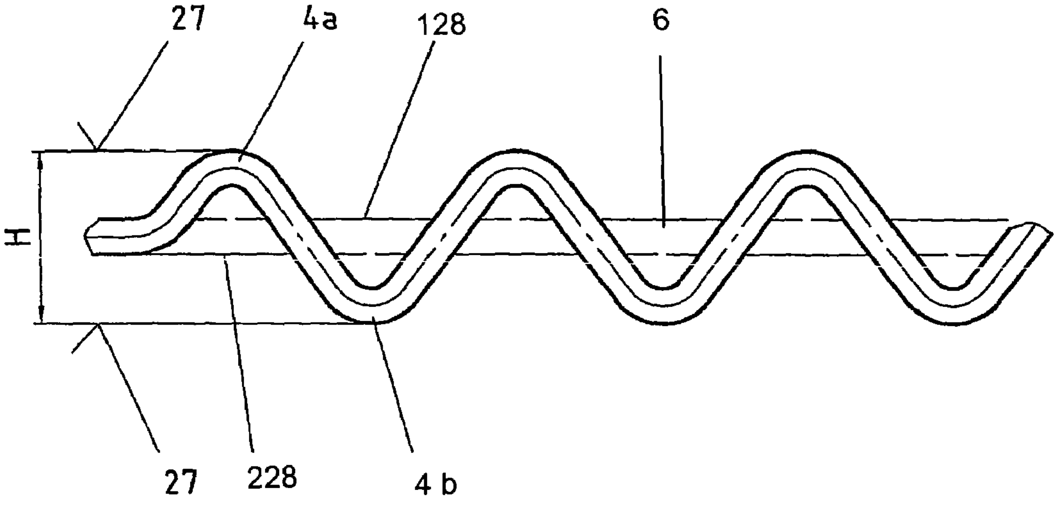
FIG. 2 shows the cross-section of a three-dimensionally formed non-woven fabric formed according to the present invention along section line A-A

A top view of the 3D embossed non-woven fabric 1 is shown in FIG. 1. Arrow 2 indicates the machine direction. The non-woven fabric is made up of fibers 3 oriented in machine direction 2, which are bonded together by known methods. In machine direction 2, non-woven fabric 1 has two continuously repeating zones 5, 7 and area 6, zones 5 and 7 having a 3D embossing and area 6 positioned between zones 5 and 7 remaining in the unembossed condition. Elevations 4*a* of zones 5 alternate with indentations (valleys) 4*b*. Within zones 7, elevations 8*a* and indentations 8*b* are situated in such a way that there is, for example, a gap between them and elevations 4*a* and indentations 4*b* of zone 5. Non-woven fabric 1 thus includes two surfaces, the elevations forming one surface and the indentations forming the other one. FIG. 2 shows a section along line A-A and the view of this section transverse to machine direction 2. The undulated 3D structure formed by consecutive arc-shaped elevations 4*a* and indentations 4*b* is shown in the foreground. Behind these undulations, unembossed areas 6 with unembossed surfaces 128, 228 extend in machine direction 2. A second wavy line, which is indicated by elevations 8*a* and valleys 8*b*, extends behind areas 6. There is a gap between 8*a* and 8*b* and 4*a* and 4*b*, respectively. As shown in FIG. 2, the tops of elevations 4*a* form an imaginary plane 27, and the tops of indentations or valleys 4*b* form a second imaginary plane 127.

Figure 3:
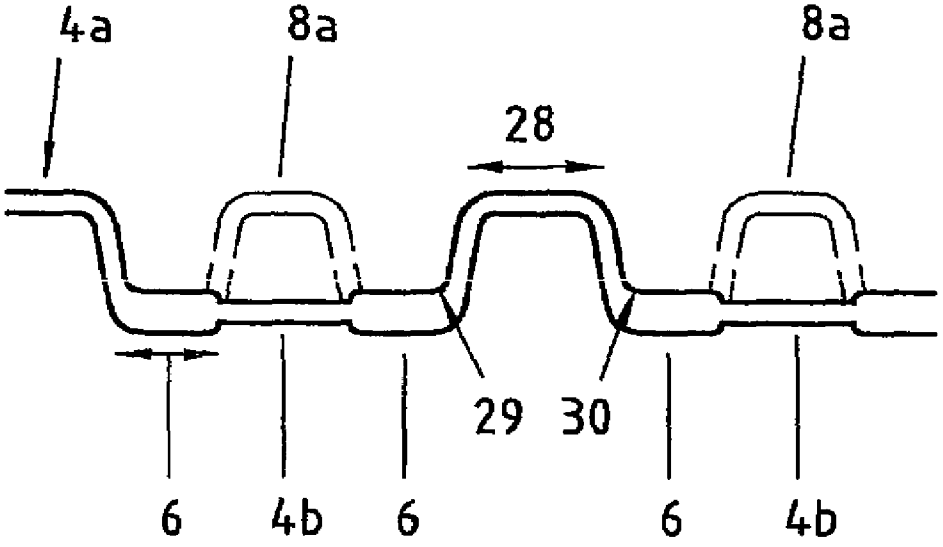
FIG. 3 shows the cross-section of a three-dimensionally formed non-woven fabric formed according to the present invention along section line B-B

FIG. 3 shows the section along line B-B (i.e., transverse to machine direction 2) as the foreground and the view in machine direction 2 as the background (dashed lines). The mass per unit area of unmolded areas 6 is significantly higher than the mass of adjacent zones 5 and 7. The mass per unit area of 3D embossed zones 5 and 7 is reduced by the factor obtained by dividing distance 28 by the perimeter from point 29 to point 30. If, for example, the mass per unit area of the unembossed non-woven fabric is 60 $g/m^2$, distance 28 has a length of 6 mm and the perimeter from point 29 to 30 has a length of 15 mm, the weight for the 3D embossed zones along its surfaces is 24 $g/m^2$, corresponding to a significant thinning of material by 60% fiber mass within the embossed zones. The higher mass per unit area in zones 6 in conjunction with the undamaged fiber bonds at that location gives rise to the advantageous property of the non-woven fabric that, without requiring an additional stabilizing layer, it generally returns to its original shape after a preceding compression better than all previously known designs with the consequence that the non-woven fabric is better suited for the acquisition of fluids of varying composition or the transport of the fluids into an absorbent layer.

Figure 4:
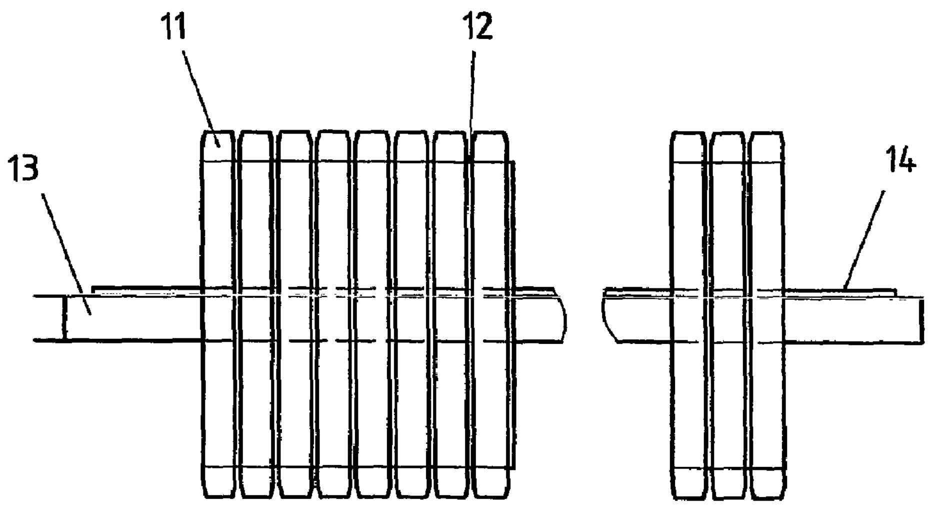
FIG. 4 shows a schematic representation of an embossing roller

An embossing roller 21 is shown in FIG. 4. A toothed wheel disk 11 and an untoothed spacer disk 12 having a smaller diameter are placed in alternation on a shaft 13 provided with a clamping wedge 14.

Figure 5:
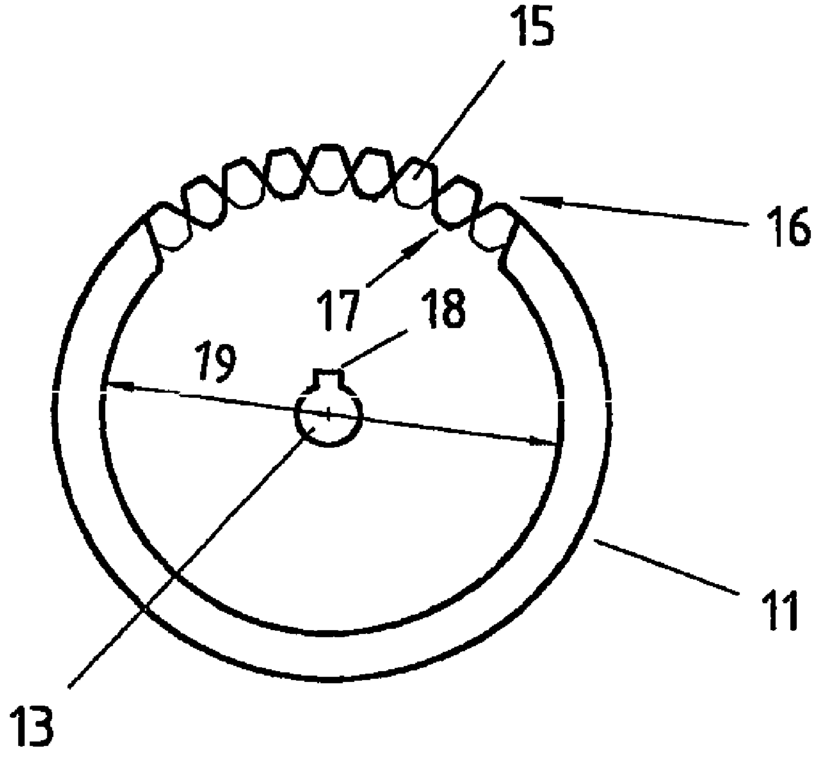
FIG. 5 shows the cross-section through an embossing roller

The diameter of disk 12 corresponds to the diameter of toothed wheel disk 11 at its deepest points 17 (the valleys). A cross-section of such an embossing roller 21 is shown in FIG. 5. Teeth 15 of front toothed wheel disk 11 have elevations 16 and indentations 17. An untoothed disk 12 having diameter 19 is placed on shaft 13 including its groove 18 (not visible) behind toothed wheel disk 11.

Figure 6:
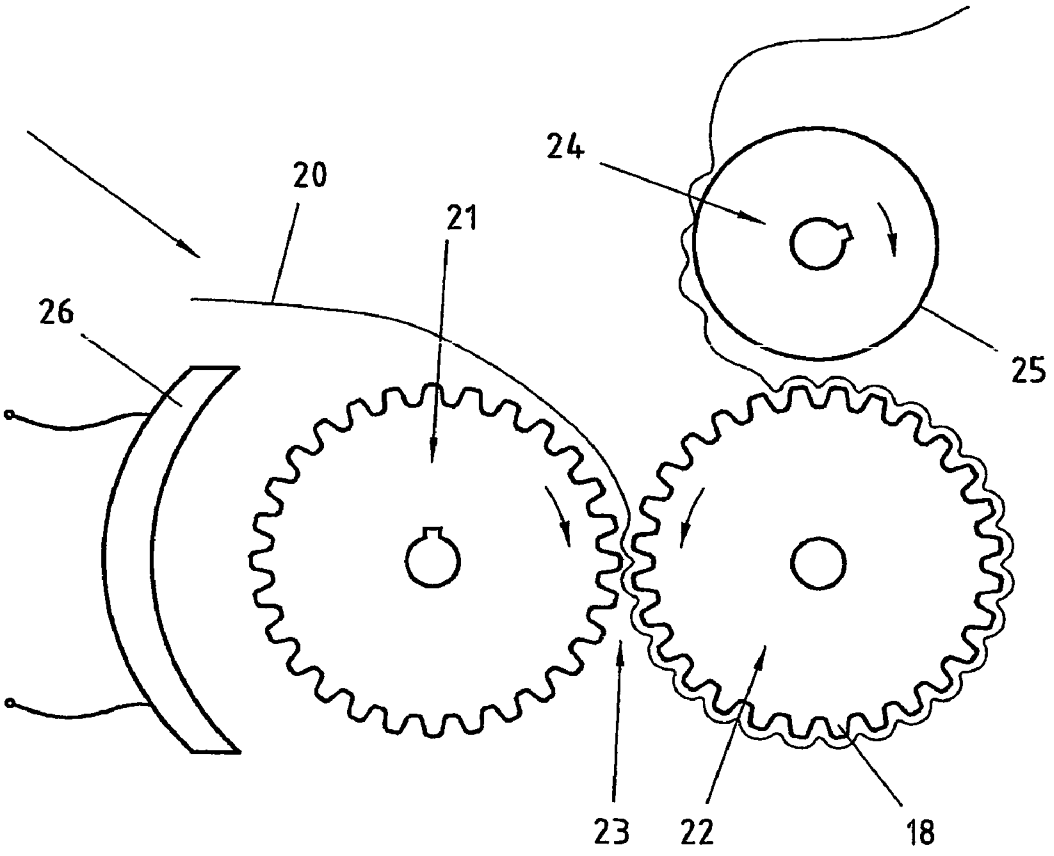
FIG. 6 shows a schematic representation of a device according to the present invention

According to FIG. 6, an embossing unit is made up of at least two meshing embossing rollers 21 and 22. At least one of the two is heatable. A heat source 26 may additionally be installed to heat the roller surface. Unembossed non-woven fabric web 20 passes the meshing teeth of both embossing rollers 21 and 22 in area 23 and is molded, favored by heat, into a 3D embossed non-woven fabric of the novel surface structure. Delivery roller 24 has a rough surface 25, which favors the further transport of the sheet product.

The embossing device may be operated at a maximum width of approximately 220 cm. In a narrower embodiment having roller widths between approximately 55 cm to 125 cm, preferably between 65 cm and 90 cm, it may be integrated into diaper machines. This is a particular embodiment of the method, which has the advantage of delivering flat roll products cut into discs and eliminating the logistic problem of placing the tapes into cartons (festooning) or cost-intensive, crosswise winding (spooling).

The method according to the present invention, including the special embodiment of embossing in the diaper machine, has the further advantage that the unembossed non-woven fabric having a fluid acquisition and distribution function may be more strongly compressed than one not subjected to 3D embossing. An unembossed rolled product always has the problem that stronger thickness compression takes place in the roll core in the vicinity of the core than in the outer area, which is not completely equalized even after placement in the diaper. A master roll having a 3 inch core as an inner diameter, having bonded acquisition and distribution non-woven fabric wound on an outer diameter of 114 cm results in approximately 2,500 to 3,000 linear meters per roll. A lower winding tightness might solve the compression problem in the winding core to a great extent; however, this is associated with the cost disadvantage of fewer linear meters on the roll. The method according to the present invention and the embossed, bulky finished material resulting from it permits a significantly stronger compression of the unembossed semifinished material having the advantage of eliminating the mentioned compression problem in the winding core and the logistical advantage of obtaining significantly more linear meters of length on the winding.

The unembossed non-woven fabric in the weight range from 30 to 100 $g/m^2$, preferably 40 to 80 $g/m^2$, has a thickness of 0.20 mm to 1.50 mm, preferably 0.35 mm to 1.20 mm, measured at a load of 0.5 kPA. The thickness after embossing is primarily a function of the height of the teeth, the distance between the teeth (degree of engagement=intensity of the meshing) and secondarily of the mass per unit area of the unembossed non-woven fabric. The thickness of the embossed non-woven fabric, measured across the intended areas produced by the elevations ranges from approximately 0.50 mm to approximately 5.50 mm, preferably approximately 0.900 mm through approximately 4.50 mm.

The width of zones 5 and 7 having toothed wheel embossing ranges from approximately 3.0 mm to approximately 20 mm, preferably 6 mm to 12 mm. Zones 5 and 7 may each have the same width or they may also have varying widths. Preferably, they have the same width. Areas 6 are generally less than or equal to half the sum of the width of zone 5 and zone 7 and preferably amount to only approximately 5% to approximately 25% of this sum. If, for example, a width of 7.0 mm is selected for zone 5 and 7, the width of areas 6 is only 0.7 mm to 3.5 mm. Areas 6 may have varying widths; however, they may not exceed a maximum total area of 50% and preferably range from approximately 10% to approximately 33%, relative to the total area of the embossed non-woven fabric. However, a 3D visual appearance having areas 6 of equal width is preferred in particular.

Hydrophilic binding agents (or those made absorbent by the addition of wetting agents) may be applied to the underside of the 3D embossed non-woven fabric used as an ADL. The side whose surface is defined by unembossed areas 6 and indentations 4*b* and 8*b* is understood to be the underside. Such one-sided application of a binder may be advantageous for the purpose of further 3D structure stabilization and may support a transport of the fluid in the direction of the absorbent core by increased hydrophilia.

EXAMPLE 1

A gauze of crimped polyester staple fibers having a denier of 6.7 dtex and a cut length of 51 mm is laid down in the machine direction. The gauze weight amounts to 45 g/m$^2$. The gauze is wetted with water in order to make the subsequent one-sided printing with binding agent easier. An aqueous polymer dispersion based on carboxylated styrene butadiene copolymer is used as a binding agent. The Shore hardness A of the film produced from this binding agent is approximately 90 to 95. A wetting agent, some pigment dye and dilution water are added to the 50% dispersion resulting in a "water-thinned" 40% mixture. This mixture is applied to one side of the fiber gauze using an anilox roll, the indentations of which are filled with this mixture. During drying on drying cylinders at 180° C., the binding agent partially migrates toward the side free from the application of binding agent. This results in a concentration gradient of the binding agent from one side of the non-woven fabric to the other. After drying, the product stays on the dryer until the binding points have been totally filmed. This relatively hard carboxylated styrene butadiene latex is applied in the amount of 15 g/m$^2$. This results in a fiber: binder ratio of 75:25.

The properties (thickness, repetition and the like) of this unembossed product are compared to those of an embossed product in Table 1.

This semifinished product was then subjected to embossing according to the present invention, an embossing device corresponding to FIGS. 4 through 6 having been used.

Figure 7:
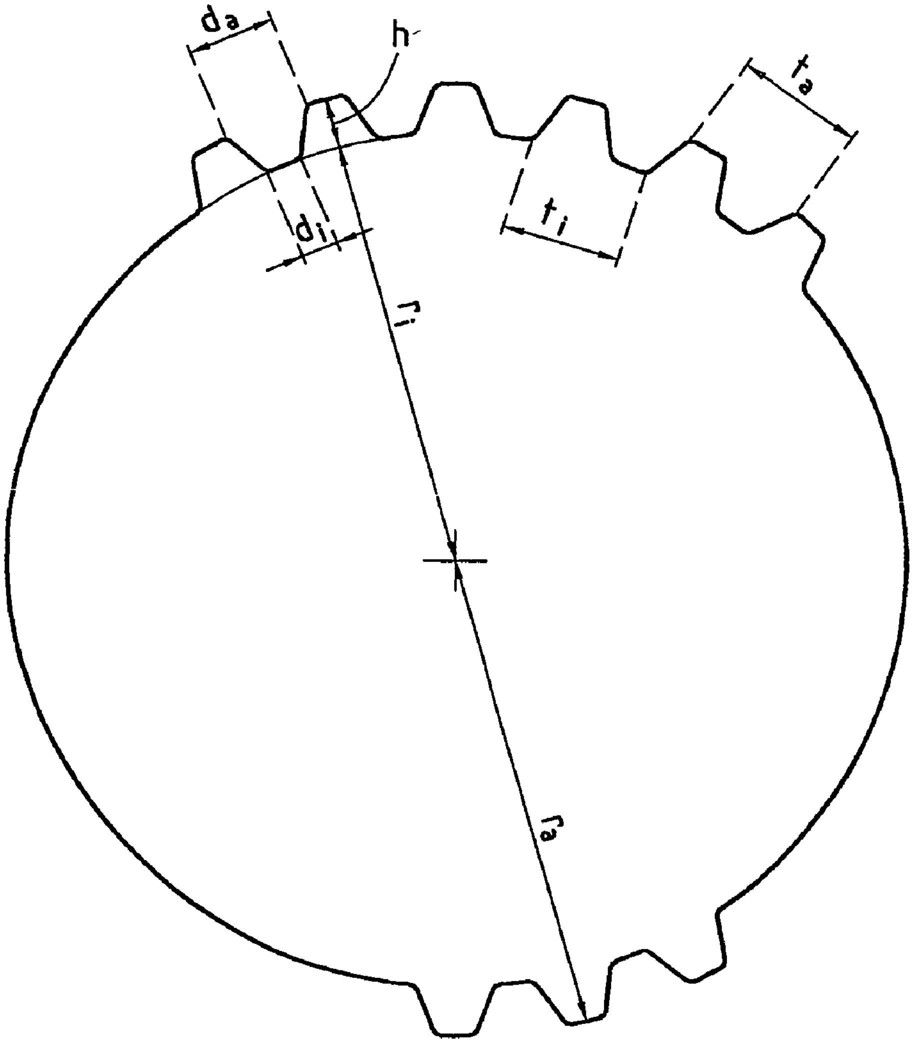
FIG. 7 shows a cross-section of a toothed wheel disk

The enlarged cross-section of a toothed wheel disk is shown in FIG. 7. $r_i$ is understood to be the internal radius of the toothed wheel and $r_a$ the external radius of the toothed wheel. Height h of the teeth is calculated as the difference between $r_a$ and $r_i$. The (curved) distance ti on the inside and ta on the outside may be calculated from the formula for circumference $u=2r\pi$. Circumferences $u_a$ and $u_i$ may be calculated by multiplying the number of teeth z on the toothed wheel having the pitch $t_i$ and $t_a$, respectively:

$$u_a=zt_a \text{ and } u_i=zt_i.$$

In examples 1, 2, embossing rollers having toothed wheels of the following dimensions and shape are used:

Z=28

$r_i$=35 mm $r_a$=37.5 mm

The following values for $t_i$ and $t_a$ are calculated using the above mathematical relationships: $t_i$=7.85 mm and $t_a$=8.41 mm As a result of the tapering of the teeth toward the outside of the roller and the circular diameter of the roller, the following relationship applies to distances $d_i$ and $d_a$.

$d_a>d_i$

In Example 1, the ratio of $d_a:d_i$ amounts to 2.88:1.0.

The width of spacer 12 (see FIG. 4) is 0.20 mm and the width of the toothed wheels is 0.75 mm, as a result of which unembossed area 6 amounts to approximately 20% of the total area of the non-woven fabric.

Non-woven fabric 20 weighing 60 g/m$^2$ is guided through the gap between the two meshing embossing rollers 21 and 22 at a speed of 10 m/min. (600 m/hr.). The external temperature of toothed wheel roller 11 made of SAE 1045 steel is 125° C. Toothed wheel roller 22 made of polyamide is unheated and heats up somewhat during the run. Additional heat source 26 ensures that the temperature on the steel roller drops. Delivery roller 24 is cooled. Subsequently, the product is rolled up with as little tensile stress as possible.

EXAMPLE 2

The procedure is the same as in Example 1 except that the gauze weight is reduced to 31 g/m$^2$. The binding agent is applied in the amount of 12 g/m$^2$, which corresponds to a fiber: binder ratio of approximately 73:27.

The 3D embossing is performed as in Example 1.

COMPARATIVE EXAMPLE 1

The binder-bonded non-woven fabric manufactured in FIG. 1 weighing 60 g/m$^2$ is subjected to embossing according to the related art. To this end, a roller pair is manufactured without having spacer disks 12 placed on the cone between the toothed wheel disks and in which all the toothed wheel disks have the same position, i.e., they are not turned to have a gap. The tooth depth is selected as in Example 1.

The binder-bonded non-woven fabric weighing 60 g/m$^2$ manufactured in FIG. 1 is embossed under the conditions of Example 1.

This conventionally embossed reference pattern having a type of undulation corresponding roughly to that of corrugated cardboard is checked for thickness, recovery capacity and creep resistance. The results of the reference pattern, of the unembossed semifinished product and the pattern of Example 1 are compared in Table 1.

Testing Methods Applied

- Liquid strike-through time according to EDANA 150.3-96 (Lister tester)
- Coverstock rewet (also known as wet back) according to EDANA 151.1-96

Strike-through times were measured after the 1$^{st}$, 2$^{nd}$ and 3$^{rd}$ application of fluid and the rewet after the 3$^{rd}$ application of fluid.

The results of Examples 1 and 2 of the unembossed and the embossed binder-bound non-woven fabric as arithmetic means from three single measurements each are compiled in Table 1.

TABLE 1

Liquid strike-through and rewet measured directly on the test object (outside of the diaper) according to the EDANA method and using the Lister test apparatus

| Test object | Liquid strike-through time(s) after $1^{st}$, $2^{nd}$, and $3^{rd}$ application of fluid: 1 time | 2 times | 3 times | Rewet (g) |
|---|---|---|---|---|
| Example 1 unembossed | 0.91 | 1.92 | 2.21 | 0.07 |
| Example 1 embossed | 0.04 | 0.01 | 0.10 | 0.06 |
| Example 2 unembossed | 0.03 | 0.69 | 0.94 | 0.08 |
| Example 2 embossed | 0.00 | 0.02 | 0.02 | 0.04 |

The results shown in Table 1 make it clear that the liquid strike-through time in particular of the embossed non-woven fabric of the present invention is significantly lower (better) than in the unembossed condition. In the case of rewet as well, improvements are noted that turn out, however, to be less significant than for the liquid strike-through time. In the Kanga test, performed on one diaper (see Table 2), the rewet results are, however, significantly better than for the EDANA-Lister test.

Liquid strike-through time using the Kanga test of Stockhausen S.OSSE.204-3.0, measured on one diaper:

A commercially available maxi plus size diaper without an acquisition and distribution layer is opened and the test object is placed between the absorbent core and the top sheet as an acquisition and distribution layer. The diaper is then reclosed and subjected to the Kanga test in this manner. 120 ml of a 0.90% saline solution per sample (synthetic urine) is used as a test liquid. After the diaper is centered between the round (corresponding to body shape) plastic body and the fabric tape surrounding it, the plastic body is loaded using a weight of 12.5 kg. Subsequently, 120 ml of the liquid is poured into the perpendicularly oriented (for girl, unisex) cylinder of the test apparatus and the time until the liquid is totally soaked into the diaper is measured (strike-through time 1).

After an approximately 20 minute waiting time, a second (strike-through time 2) and a third measurement (strike-through time 3) are performed using the same quantity of liquid (120 ml).

Rewet using the Kanga test of Stockhausen S.OSSE.204-3.0, measured on one diaper:

To determine the rewet properties, after the third quantity of liquid is totally soaked in and an additional waiting time of 20 minutes, the diaper is removed from the measuring apparatus and spread out on a table. A weighed stack of 3 filter papers of approximately 40 g/m$^2$ each is placed on the liquid entry point of the diaper and loaded by 1270 g (corresponding to a pressure load of approximately 20 g/cm$^2$). After 20 minutes, the filter paper stack is reweighed. The lower the value, the dryer the baby's skin stays.

TABLE 2

Results for strike-through time and rewet determined according to the Kanga method

| Maxi plus size diaper | Kanga test: Strike-through time(s) after $1^{st}$, $2^{nd}$, $3^{rd}$ application of liquid: 1 time | 2 times | 3 times | Rewet (g) |
|---|---|---|---|---|
| Brand name diaper No. 1 - original condition | 13.5 | 27.5 | 34.0 | 37.2 |
| Brand name diaper No. 1 - opened | 11.3 | 25.5 | 33.0 | 31.5 |
| Brand name diaper No. 2 - original condition | 13.5 | 33.5 | 43.3 | 11.9 |
| Brand name diaper No. 2 - opened | 14.0 | 52.3 | 60.0 | 0.44 |
| Brand name diaper No. 3 - original condition | 22.2 | 30.3 | 53.5 | 16.1 |
| Brand name diaper No. 3 - opened | 23.1 | 47.9 | 65.2 | 20.9 |
| Diaper having embossed ADL from Example 1 | 5.3 | 9.5 | 12.1 | 0.28 |

Table 2 shows that the non-woven fabric of the present invention displays significantly better properties when installed in a diaper as an ADL.

Creep Resistance CR

To determine creep resistance CR, samples sized approximately 7 cm×7 cm were punched out and maintained at a constant temperature in the laboratory for 25 hours. Three single measurements were taken in each case to determine an arithmetic mean.

A load of 7.2 kPa is placed on the test object for 72 hours at 45° C. The place to be loaded is marked. Subsequently, the sample is removed from the oven and unloaded for 2 minutes. The thickness is then measured at a pressing pressure of 0.5 kPa and a pressing pressure area of 25 cm$^2$. The thickness was measured again after an unloading time of 2 hours and 24 hours.

TABLE 3

Thickness measurement after thermal storage (creep resistance KB) and after varying unloaded recovery times

| Test object | Initial thickness before loading at 45° C. mm at 0.5 kPa | After 72 hours storage at 45° C. and 7.2 kPa and a recovery time of: t = 0 mm at 0.5 kPa | t = 2 hr. mm at 0.5 kPa | t = 24 h hr. mm at 0.5 kPa |
|---|---|---|---|---|
| Example 1 unembossed | 0.92 | 0.59 | 0.63 | 0.68 |
| Example 1 3D embossed | 2.56 | 0.67 | 0.72 | 0.91 |
| Reference | 1.87 | 0.51 | 0.54 | 0.60 |

The starting thickness of the reference sample having conventional embossing (undulation) displays a significantly lower thickness after a loading of 0.5 kPa than Example 1, which is 3D embossed according to the method of the present invention.

Specific Volume (SV)

Thicknesses d were measured at loads of 0.50 kPa and 6.2 kPa. The following calculation is used to determine the value for specific volume in cm$^3$/g (the reciprocal value of specific bulk density):

$$SV=(d/FG)\times 1000\ in\ (cm^3/g)$$

FG being the mass per unit area of the non-woven fabric in $g/m^2$ and d the thickness in mm.

TABLE 4

Specific Volume

| Test object | Specific volume ($cm^3/g$) at 0.5 kPa | Specific volume ($cm^3/g$) at 6.2 kPa | Relative specific Volume (%) at 0.5 kPa | Relative specific Volume (%) at 6.2 kPa |
|---|---|---|---|---|
| Example 1 unembossed | 15.3 | 11.6 | 100 | 100 |
| Example 1 3D embossed | 42.6 | 14.7 | 278 | 127 |

The values shown for specific volume in Table 4 show that an improved non-woven fabric having a significant fluid acquisition function has been created using the 3D embossing according to the present invention.

What is claimed is:

1. A three-dimensionally embossed non-woven fabric having a first side and a second side and a manufacturing machine direction comprising:

fibers or filaments;

the first and second sides being provided with zones having regularly or irregularly alternating elevations and indentations, the elevations and indentations being transverse to the machine direction and the zones being separated from one another by unembossed, continuous areas extending in the machine direction, the unembossed, continuous areas constituting a proportion ranging from 5% to 50% with respect to the surface area of the non-woven fabric, the elevations when viewed in cross-section, being formed by a prolongation on both sides of the unembossed, continuous areas such that the fibers or filaments that form the elevations are stretched away from the unembossed continuous areas such that the fabric is thinner at the elevation than at the unembossed continuous areas.

2. The fabric as recited in claim 1 wherein tops of the elevations and indentations on both sides define imaginary planes, the imaginary planes having a distance H of 0.5 mm to 5.5 mm from one another.

3. The fabric as recited in claim 1 wherein tops of the elevations and indentations on both sides define imaginary planes, the imaginary planes having a distance of 0.9 mm to 4.5 mm from one another.

4. The fabric as recited in claim 1, wherein the unembossed, continuous areas occupy a proportion of 10% to 33% relative to the surface area of the non-woven fabric.

5. The fabric as recited in claim 1 wherein the fibers or filaments are primarily oriented in the machine direction.

6. The fabric as recited in claim 1 wherein the elevations and indentations of adjacent zones are arranged in a grid-like pattern.

7. The fabric as recited in claim 1 wherein the elevations and indentations of adjacent zones are arranged so that the elevations and indentations are arranged symmetrically on both sides of the unembossed, continuous areas.

8. The fabric as recited in claim 1 wherein the elevations and indentations of adjacent zones have a clearance on both sides of the unembossed, continuous areas, viewed in the machine direction.

9. The fabric as recited in claim 1 wherein the elevations and indentations of adjacent zones are asymmetrically displaced in relation to one another on both sides of the continuous areas viewed in the machine direction.

10. A method for manufacturing a non-woven fabric as recited in claim 1 comprising the steps of:

forming a flat non-woven fabric comprised of fibers or filaments primarily oriented in a manufacturing machine direction so that the fibers or filaments of the non-woven fabric are bonded together; and subsequently subjecting the non-woven fabric to the action of at least one embossing roller at a temperature ranging from 65° C. to 160° C. so as to form a three-dimensional non-woven fabric, the unembossed, continuous areas extending in the machine direction.

11. The method as recited in claim 10 wherein the fibers or filaments are bonded by a binding agent.

12. The method as recited in claim 11 wherein the binding agent is applied to one side of the non-woven fabric.

13. The method as recited in claim 11 wherein a wetting agent is added to the binding agent.

14. The method as recited in claim 11 further comprising providing a second application of the binding agent to the unembossed, continuous areas for reinforcement.

15. The method as recited in claim 14 wherein the second application of binding agent is performed by spraying or imprinting onto the unembossed, continuous areas.

16. The method as recited in claim 14 wherein the second application of binding agent is applied to both sides of the unembossed, continuous areas.

17. A device for implementing the method as recited in claim 10 comprising:

at least two embossing rollers meshing with one another so that the non-woven fabric may be passed between them and shaped, the embossing rollers including toothed wheels situated on a shaft and being separated from one another by spacers, the unembossed, continuous areas extending in the machine direction.

18. The device as recited in claim 17 wherein the toothed wheels have straight or oblique teeth.

19. The device as recited in claim 17 wherein the toothed wheels of embossing rollers are made of iron, copper, aluminum, or alloys thereof or of polymers.

20. The device as recited in claim 17 wherein the toothed wheel of one of the embossing rollers is made of aluminum and the toothed wheel of an other of the embossing rollers is made of polyamide.

21. The device as recited in claim 17 wherein only one embossing roller is heated.

22. The device as recited in claim 17 wherein a thermal radiator is provided for the heating.

23. A method for manufacturing the fabric as recited in claim 1 comprising manufacturing the fabric in the machine direction, the unembossed, continuous areas extending in the machine direction.

24. The fabric as recited in claim 1 wherein the elevations and indentations of adjacent zones are arranged so that the elevations of each zone are aligned parallel to the indentations of the adjacent zones.

25. The fabric as recited in claim 1 wherein a mass per unit area of the elevations and indentations of adjacent zones is lower than the mass of the unembossed areas.

26. The fabric as recited in claim 1 wherein a mass per unit area of the elevations and indentations of adjacent zones is 60% lower than the mass of the unembossed areas.

27. The fabric as recited in claim 1 wherein the fibers or filaments are polymers.

28. The fabric as recited in claim 27 further comprising a hydrophilic, easy-to-wet, surface-active agent.

29. The fabric as recited in claim 27 wherein the fibers or filaments include crimped synthetic fibers.

30. A hygiene product including:

an acquisition and distribution layer including the fabric as recited in claim 1; and an absorbent core lying under the acquisition and distribution layer.

* * * * *

UNITED STATES PATENT AND TRADEMARK OFFICE

CERTIFICATE OF CORRECTION

PATENT NO. : 7,678,442 B2
APPLICATION NO. : 10/496048
DATED : March 16, 2010
INVENTOR(S) : Casey et al.

It is certified that error appears in the above-identified patent and that said Letters Patent is hereby corrected as shown below:

Title Page, Item (73) Assignee should read: Carl Freudenberg KG, Weinheim (DE)

Signed and Sealed this
Thirty-first Day of May, 2011

David J. Kappos

David J. Kappos
*Director of the United States Patent and Trademark Office*